United States Patent [19]

Engel

[11] 4,429,149

[45] * Jan. 31, 1984

[54] 4-PHENYL-2-INDANYL ESTERS OF 1R,CIS-3-(2-HALO-3,3,3-TRIFLUORO-PROPENYL)-2,2-DIMETHYLCYCLO-PROPANECARBOXYLIC ACID

[75] Inventor: John F. Engel, Washington Crossing, Pa.

[73] Assignee: FMC Corporation, Philadelphia, Pa.

[*] Notice: The portion of the term of this patent subsequent to Apr. 21, 1998 has been disclaimed.

[21] Appl. No.: 370,217

[22] Filed: Apr. 20, 1982

Related U.S. Application Data

[63] Continuation-in-part of Ser. No. 221,656, Dec. 31, 1980, Pat. No. 4,333,950, which is a continuation-in-part of Ser. No. 42,372, May 24, 1979, Pat. No. 4,263,319, which is a continuation-in-part of Ser. No. 927,198, Jul. 24, 1978, abandoned, which is a continuation-in-part of Ser. No. 870,973, Jan. 20, 1978, abandoned.

[51] Int. Cl.$^3$ .............................................. C07C 69/743
[52] U.S. Cl. ................................... 560/124; 424/305
[58] Field of Search ......................................... 560/124

[56] References Cited

U.S. PATENT DOCUMENTS

| 4,263,319 | 4/1981 | Engel | 560/124 |
| 4,333,950 | 6/1981 | Engel | 560/124 |
| 4,362,744 | 12/1982 | Plummer | 560/124 |

*Primary Examiner*—Michael L. Shippen
*Attorney, Agent, or Firm*—Robert M. Kennedy; H. Robinson Ertelt; Robert L. Andersen

[57] ABSTRACT

Insecticidal 4-phenyl-2-indanyl 1R,cis-3-(2-halo-3,3,3-trifluoro-1-propenyl)-2,2-dimethylcyclopropanecarboxylates having a racemic or optically active indanyl moiety, methods of preparation and use, and efficacy data against representative insect species are disclosed and exemplified.

10 Claims, No Drawings

4-PHENYL-2-INDANYL ESTERS OF 1R,CIS-3-(2-HALO-3,3,3-TRIFLUOROPROPENYL)-2,2-DIMETHYLCYCLOPROPANECARBOXYLIC ACID

The present application is a continuation-in-part of co-pending application U.S. Ser. No. 221,656, filed Dec. 31, 1980, issued June 8, 1982 as U.S. Pat. No. 4,333,950, which is a continuation-in-part application of U.S. Ser. No. 043,372, filed May 24, 1979 issued as U.S. Pat. No. 4,263,319 on Apr. 21, 1981, which is a continuation-in-part of U.S. Ser. No. 927,198, filed July 24, 1978, abandoned, which is a continuation-in-part of U.S. Ser. No. 870,973, filed Jan. 20, 1978, abandoned, the disclosures of all of which are incorporated herein by reference.

The invention described in this application pertains to insecticidal or acaricidal pyrethroid esters derived from racemic or optically active 4-phenyl-2-indanol and 1R,cis-3-(2-halo-3,3,3-trifluoropropenyl)-2,2-dimethylcyclopropanecarboxylic acid.

Pyrethrins, naturally occurring extracts of crysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. A significant advance in pyrethroid acid research was the discovery by Elliott et al. of a highly active group of compounds in which the acid moiety is a 3-(2,2-dihaloethenyl)-2,2-dimethylcyclopropanecarboxylic acid residue. More recently it has been found that replacement of one of the halogen atoms on the ethenyl group with a perhaloalkyl group, particularly trifluoromethyl, results in compounds which have substantially improved insecticidal properties over the corresponding dihaloethenyl compounds. The parent applications referred to above disclose, inter alia, 4-phenyl-2-indanyl 3-[2-halo-2-(perhaloalkyl)ethenyl]-2,2-dimethylcyclopropanecarboxylates, and describe generally the various possible isomeric and steric configurations of such compounds.

The prior applications above also disclose the fact that certain isomers of the disclosed compounds are generally more active insecticidally than other isomers or isomer mixtures. Esters of (+)-4-phenyl-2-indanol are disclosed as being generally more active than the corresponding esters prepared with the racemic or levorotatory alcohol. Esters of the cis isomer (1,3-cis) of cyclopropanecarboxylic acids are disclosed as being generally superior insecticidally to the corresponding esters of the trans isomer or cis,trans mixture of isomers, the 1R,cis isomer esters generally being more active than the corresponding 1S,cis isomer esters.

It has now been discovered that for 4-phenyl-2-indanyl 3-(2-halo-3,3,3-trifluoro-1-propenyl)-2,2-dimethylcyclopropanecarboxylate, the 1S,cis isomer is, for all practical purposes, devoid of insecticidal activity, and the 1R,cis isomer has, for the most part, greatly enhanced insecticidal efficacy over the racemic cis (1R,S) mixture.

In this application, the term "lower" as applied to an aliphatic hydrocarbon group means having 1 to 6 carbon atoms, preferably 1 to 4 carbon atoms. The term "halo" or "halogen" means bromine, chlorine or fluorine. The term "haloalkyl" means an alkyl group of 1 to 3 carbon atoms substituted with one or more halogen atoms. The term "insecticide" is used in its broadest sense and includes compounds possessing activity against true insects, acarids, and other household, veterinary or crop pests of the phylum Arthropoda. The term "enantiomeric excess" or "EE" is used herein to describe the isomer composition of 4-phenyl-2-indanol or the 4-phenyl-2-indanyloxy moiety of the present compounds, and is the percent excess of one enantiomer over the other in a mixture containing the two possible enantiomers in accordance with the formula $$\% EE = \frac{X - Y}{X + Y} \cdot 100$$

where X is the concentration of the more abundant enantiomer in the mixture, and Y is the concentration of the less abundant enantiomer. An enantiomeric excess of 100% means that for all practical purposes only one of the two enantiomers is present. These definitions are applicable throughout the specification and claims except where a contrary meaning is clearly indicated.

Accordingly, the present invention provides a 4-phenyl-2-indanyl 1R,cis-3-(2-halo-3,3,3-trifluoro-1-propenyl)-2,2-dimethylcyclopropanecarboxylate of formula I

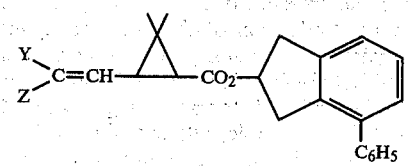

wherein one of Y and Z is a halogen atom, preferably chlorine, and the other is a trifluoromethyl group. The absolute configuration of the 1R,cis acid moiety is shown in the following partial formula:

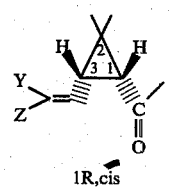

1R,cis

The alcohol moiety may be racemic or optically active. If optically active, it need not be optically pure; one isomer may be present in an enantiomeric excess of less than 100% over the other. The dextrorotatory or (+) isomer is preferred, and will advantageously be present in an enantiomeric excess of at least 25%, preferably at least 60%, over the levorotatory isomer. (+)-4-Phenyl-2-indanol and esters thereof are described in detail in the parent application, U.S. Ser. No. 221,656, supra. The dextrorotatory isomer of the 4-phenyl-2-indanyloxy moiety, and of 4-phenyl-2-indanol itself, is the isomer having the S absolute configuration at C-2 of the indane ring. The corresponding levorotatory isomer has the R configuration at C-2. The R and S configurations of the alcohol moiety are those shown in the following formulas:

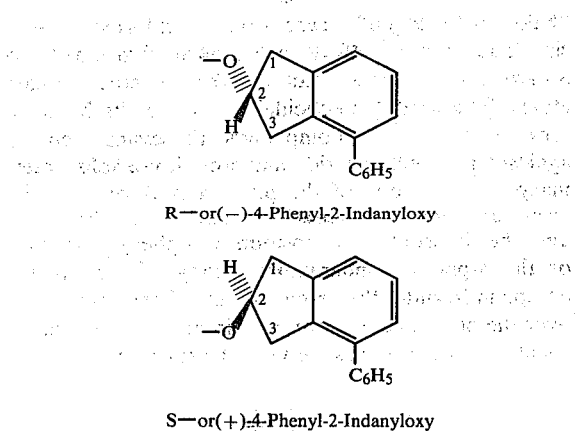

R—or(−)-4-Phenyl-2-Indanyloxy

S—or(+)-4-Phenyl-2-Indanyloxy

The compounds of this invention may be prepared by methods analogous to those known in the art for similar compounds, for example, by combining under esterification conditions the appropriate isomer or isomer mixture of 4-phenyl-2-indanol and 1R,cis-(2-halo-3,3,3-trifluoropropenyl)-2,2-dimethylcyclopropanecarbonyl chloride.

Racemic 4-phenyl-2-indanol may be prepared by the method disclosed in U.S. Pat. No. 4,263,319, spura, or by various other methods. In the method described in the patent, 2-biphenylmethanol is converted in several steps to 7-phenyl-1H-indene, which is then treated with hydrogen peroxide and formic acid to give, after steam redistillation in the presence of dilute sulfuric acid, 4-phenyl-2-indanone. Reduction of the 2-indanone with sodium borohydride in ethanol gives the corresponding 2-indanol. 7-Phenyl-1H-indene can serve as the starting material in other methods for preparing racemic 4-phenyl-2-indanol. For example, either the hydroboration-oxidation or the epoxidation-reduction of 7-phenyl-1H-indene will give 4-phenyl-2-indanol.

The preparation of (+)-4-phenyl-2-indanol, by chiral synthesis from 7-phenyl-1H-indene, is disclosed in the copending parent case U.S. Ser. No. 221,656, supra. This method involves the hydroboration-oxidation of 7-phenyl-1H-indene wherein the hydroboration step is conducted in the presence of an optically active hydroborating agent prepared from (+)-α-pinene and borane. (−)-4-Phenyl-2-indanol can be prepared by an analogous method using (−)-α-pinene as described in Example 3 below.

1R,cis-3-(2-Halo-3,3,3-trifluoropropenyl)-2,2-dimethylcyclopropanecarbonyl chloride is readily prepared from the corresponding free acid by treatment with a chlorinating agent such as oxalyl chloride or thionyl chloride. The free acid itself may be prepared by resolution of the corresponding racemic cis acid with an optically active amine, for example, (−)-α-phenylethylamine. The resolution process is more fully described in Example 7 below.

The examples which follow illustrate preparation of the compounds of this invention and methods for determining the insecticidal efficacy of them. In the examples, all temperatures are in degrees Celsius, all pressures are in mm Hg, and reduced pressure for concentrations of liquid was produced by a water aspirator unless otherwise specified. The enantiomeric excess percentages for 4-phenyl-2-indanol were calculated from peak heights obtained from an nmr analysis of the acetate derivatives in the presence of a chiral shift reagent. The shift reagent used was tris-[3-(heptafluoropropylhydroxymethylene)-d-camphorato], europium (III) derivative, [Eu(hfc)3]. The heights of the peaks for the methyl protons from the acetyl groups were used as the concentration figures in the formula $$\% EE = \frac{X - Y}{X + Y} \cdot 100.$$

It is difficult to accurately determine EE's greater than about 95% by the chiral shift reagent method. Therefore, values in the range of 95% to 100% are expressed simply as being ≧95%.

Example 1 illustrates the preparation of racemic 4-phenyl-2-indanol.

EXAMPLE 1

Synthesis of Racemic 4-Phenyl-2-Indanol

A. Preparation of 2-(bromomethyl)biphenyl

A stirred solution of 58.9 g (0.319 mole) of 2-biphenylmethanol and 6 ml of concentrated sulfuric acid in 67 ml of aqueous 48% hydrobromic acid was heated under reflux for 5 hours. The reaction mixture was cooled to ambient temperature, poured into ice-water, and the resulting mixture extracted with three portions of 100 ml each of diethyl ether. The combined extracts were washed with 50 ml of a saturated aqueous solution of sodium bicarbonate, then with 50 ml of water. The organic layer was dried with magnesium sulfate, filtered, and the filtrate concentrated under reduced pressure to give 76.8 g of 2-(bromomethyl)biphenyl as a residual oil. The nmr and ir spectra were consistent with the proposed structure.

B. Preparation of diethyl (2-phenylbenzyl)malonate

A stirred mixture of 12.5 g (0.54 mole) of sodium hydride (25 g of a 50% dispersion in mineral oil) in 300 ml of dimethylformamide and 900 ml of benzene was placed under a nitrogen atmosphere and cooled to 0° C. To this mixture, 104.3 g (0.9 mole) of diethyl malonate was added dropwise during 5 minutes, and the mixture was stirred until hydrogen evolution ceased. 2-(Bromomethyl)biphenyl (117 g, 0.47 mole) was then added at 0° C. Upon complete addition, the reaction mixture was stirred at 0° C. for 30 minutes, then was allowed to warm to ambient temperature with stirring for one hour. The reaction mixture was poured into 500 ml of water, the layers separated, and the aqueous layer washed with two portions of 250 ml each of diethyl ether. The organic layer was combined with the ether washings, and the whole was washed with one portion of 500 ml of aqueous 5% hydrochloric acid, one portion of 500 ml of water, one portion of 300 ml of a saturated aqueous solution of sodium bicarbonate, and finally, one portion of 500 ml of water. The organic layer was dried with magnesium sulfate, filtered, and the filtrate concentrated under reduced pressure to give an oil residue. The oil was distilled under reduced pressure to give 149.0 g of diethyl (2-phenylbenzyl)malonate; b.p. 175°–180° C./0.8–0.9 mm. The nmr spectrum was consistent with the proposed structure.

C. Preparation of (2-phenylbenzyl)malonic acid

A stirred solution of 149.0 g (0.456 mole) of diethyl (2-phenylbenzyl)malonate and 56.1 g (1.0 mole) of potassium hydroxide in 50 ml of water and 500 ml of ethanol was heated under reflux for 3 hours. The reaction mixture was allowed to cool to ambient temperature and stand for 60 hours. The ethanol was removed by distillation, and the residue slurried in 400 ml of water. The mixture was extracted with one portion of 250 ml of diethyl ether. The aqueous phase was separated and acidified with concentrated hydrochloric acid, then extracted with two portions of 250 ml each of diethyl ether. The two ether extracts of the acidified aqueous phase were combined, dried with magnesium sulfate, filtered, and the filtrate concentrated under reduced pressure to give (2-phenylbenzyl)malonic acid as a pale yellow oil. The oil was used without further purification in the next step of this reaction sequence.

D. Preparation of 3-(2-biphenyl)propionic acid

A solution of 124.2 g (0.46 mole) of the oil from step C of this Example in 500 ml of water as heated under reflux for 16 hours. The reaction mixture was cooled, and the product was collected by filtration to give, after recrystallization from ethanol-water, 92.9 g of 3-(2-biphenyl)propionic acid. The nmr spectrum was consistent with the proposed structure.

Analysis calc'd for $C_{15}H_{14}O_2$: C 79.62, H 6.24; Found: C 79.84, H 5.98.

E. Preparation of 4-phenyl-1-indanone

A solution of 92.9 g (0.41 mole) of 3-(2-biphenyl)propionic acid in 100 ml of thionyl chloride was stirred at ambient temperature for 16 hours. The excess thionyl chloride was removed by distillation followed by co-distillation with three 50 ml portions of benzene.

The residue was dissolved in 150 ml of benzene and was added dropwise at 10° C. over 15 minutes to a stirred mixture of 71.0 g (0.53 mole) of aluminum chloride in 900 ml of benzene. Upon complete addition the reaction mixture was stirred at 10° C. for 110 minutes, then poured into 1000 ml of ice-water and stirred until the ice melted. The aqueous phase was separated and extracted with two portions of 100 ml each of diethyl ether. The ether extracts and the organic phase were combined and washed with a 10% aqueous solution of sodium hydroxide, then with two portions of water. The combined extracts were dried with magnesium sulfate, filtered, and the filtrate concentrated under reduced pressure to give, as a brown crystalline solid, 85.4 g of 4-phenyl-1-indanone, m.p. 85°–90° C. The product was used without further purification.

A sample was recrystallized for analytical purposes. The nmr spectrum was consistent with the proposed structure.

Analysis calc'd for $C_{15}H_{20}O$: C 86.50, H 5.81; Found: C 86.63, H 5.74.

F. Preparation of 4-phenyl-1-indanol

To a stirred solution of 20.8 g (0.10 mole) of 4-phenyl-1-indanone in 150 ml of ethanol was added portionwise 2.0 g (0.06 mole) of sodium borohydride. During the addition the reaction temperature rose to 33° C. Upon complete addition, the reaction mixture was allowed to cool to ambient temperature and was stirred for 16 hours. The reaction mixture was diluted with water and concentrated under reduced pressure. A precipitate, which developed during concentration of the mixture, was collected and dried, then recrystallized from toluene-hexane to give 17.3 g of 4-phenyl-1-indanol; m.p. 80.5°–81.5° C. The nmr spectrum was consistent with the proposed structure.

Analysis calc'd for $C_{15}H_{14}O$: C 85.68, H 6.71; Found: C 85.63, H 6.70.

G. Preparation of 7-phenyl-1H-indene

A stirred solution of 16.7 g (0.08 mole) of 4-phenyl-1-indanol and 0.1 g of p-toluenesulfonic acid in 180 ml of benzene was heated under reflux for one hour as by-product water was collected in a Dean-Stark trap. The reaction mixture was washed with two portions of 50 ml of a 5% aqueous solution of sodium bicarbonate, then with one portion of 50 ml of water. The organic phase was dried with magnesium sulfate, filtered, and the filtrate concentrated under reduced pressure, keeping the temperature under 50° C., to give 14.8 g of 7-phenyl-1H-indene. The nmr spectrum was consistent with the proposed structure.

Analysis calc'd for $C_{15}H_{12}$: C 93.71, H 6.29; Found: C 93.47, H 6.31.

H. Preparation of 1,2-epoxy-4-phenylindane

A stirred solution of 47.5 g (0.234 mole) of m-chloroperbenzoic acid (85% purity) in 390 ml of chloroform was cooled to 0° C. To this was added dropwise a solution of 45 g (0.234 mole) of 7-phenyl-1H-indene (which may be prepared as in Step G above) in 110 ml of chloroform. After complete addition, the mixture was stirred for 2½ hours, then was allowed to stand for 21 hours at 0° C. With the temperature in the range of 0°–5° C., 100 ml of a 10% aqueous solution of sodium hydroxide, then 50 ml of a 10% aqueous solution of sodium sulfate, were added dropwise with stirring. Afte complete addition the two-phase mixture was stirred for 30 minutes. The organic phase was separated, washed first with a dilute aqueous solution of sodium bicarbonate, then with water, dried over anhydrous sodium sulfate, and filtered. The filtrate was concentrated under reduced pressure to give 47.7 g of 1,2-epoxy-4-phenylindane as a pale yellow oil, 97% purity by gas chromatographic analysis.

I. Preparation of 4-phenyl-2-indanol

Under a dry argon atmosphere, a stirred solution of 9 g (0.067 mole) of aluminum chloride in 225 ml of anhydrous diethyl ether was cooled to 0° C. To this was added portionwise 9.4 g (0.245 mole) of lithium aluminum hydride. The cooling bath was removed, and the mixture stirred for 15 minutes. With the temperature being maintained at 25° C., a solution of 47.7 g (0.229 mole) of 1,2-epoxy-4-phenylindane in 175 ml of anhydrous diethyl ether was added dropwise. After complete addition, the mixture was heated at reflux for 18 hours, then cooled to 0° C. Water and an aqueous solution of sodium hydroxide were added to decompose the excess lithium aluminum hydride, and the mixture was filtered. The filter cake was washed with diethyl ether, and the filtrate and washes were combined and dried over anhydrous sodium sulfate. The mixture was filtered, and the filtrate concentrated under reduced pressure to give an oil. The oil was subjected to column chromatography on silica gel, eluting with 98:2 toluene/ethyl acetate followed by 90:10 toluene/ethyl acetate to give 31.5 g of 4-phenyl-2-indanol, mp 72°–76° C. The nmr spectrum was consistent with the proposed structure.

Examples 2 and 3 describe the preparation of optically active 4-phenyl-2-indanol.

EXAMPLE 2

Synthesis of (+)-4-Phenyl-2-Indanol

A. Hydroboration of 7-phenyl-1H-indene

Under a dry nitrogen atmosphere, a solution of 32 g (0.23 mole) of (+)-α-pinene in about 100 ml of tetrahydrofuran was stirred and cooled to 0° C. One hundred and twelve (112) ml of a 1.05 M solution of borane-tetrahydrofuran complex (0.118 mole) was added slowly, and the reaction mixture was stirred at 0° C. for 1 hour. To this was added dropwise a solution of 18.8 g (0.098 mole) of 7-phenyl-1H-indene in about 100 ml of tetrahydrofuran. The reaction mixture was stirred at 0° C. for 2.5 hours, then at room temperature for 2 hours. The mixture was cooled to 0° C., and 40 ml of water, 60.3 ml of a 3 N sodium hydroxide solution, and finally 60.3 ml of a 30% aqueous solution of hydrogen peroxide were added in sequence slowly. The mixture was stirred at room temperature for two days, then poured into water, and extracted with two 100 ml portions of diethyl ether. The ether extracts were washed with water, dried with anhydrous sodium sulfate, filtered, and the filtrate concentrated to give an oil. The oil was distilled using a Kugelrohr distillation apparatus (95° C./2.5 mm) to leave 17.4 g of an oily pot residue. Gas chromatographic analysis of the oily residue showed it contained 37% of 4-phenyl-2-indanol, 7% of 4-phenyl-1-indanol, and 55% of unreacted 7-phenyl-1H-indene. Nuclear magnetic resonance analysis of the acetate derivatives of the mixture using a shift reagent, Eu(hfc)$_3$, showed a 41% EE of the dextrorotatory isomer for 4-phenyl-2-indanol.

B. Separation and refinement of (+)-4-phenyl-2-indanol

A stirred solution of the product from above (containing 4-phenyl-2-indanol, 4-phenyl-1-indanol, and 7-phenyl-1H-indene) and 0.05 g of p-toluenesulfonic acid monohydrate in 80 ml of toluene was heated at reflux for 5 minutes to effect dehyration of the 1-indanol. The reaction mixture was cooled and applied to a column of silica gel. Elution was accomplished with toluene, then with 1:1 toluene/ethyl acetate to give, from appropriate fractions, 6.3 g (+)-4-phenyl-2-indanol, EE 48%.

(+)-4-Phenyl-2-indanol (3.85 g, EE 48%), from above, was finely powdered and added to 10 ml of toluene, and the mixture was stirred at room temperature for 1 hour. The insoluble material was collected on a filter paper and rinsed with a small amount (50 drops) of toluene. The collected material was dried to give 1.77 g of (+)-4-phenyl-2-indanol, mp 100°-101° C., EE 83%.

Several previously prepared samples of (+)-4-phenyl-2-indanol were combined to give 4.6 g, EE 57%. The combined sample was stirred in 15 ml of toluene at room temperature for 16 hours, and the insoluble material was collected to give 2.22 g of (+)-4-phenyl-2-indanol, mp 102°-103° C. This material was combined with 1.3 g of the EE 83% sample from above, and the process was repeated using 10 ml of toluene to give 2.9 g of (+)-4-phenyl-2-indanol, mp 102°-104° C., EE 92%.

In another run, 52.6 g of (+)-4-phenyl-2-indanol, EE 67%, gave, after successive washes with toluene, 30.4 g product, mp 103°-104° C., EE ≧95%, $[\alpha]_D^{24}$ +37.4°.

EXAMPLE 3

Synthesis of (−)-4-Phenyl-2-Indanol

A. Hydroboration of 7-phenyl-1H-indene

Under an argon atmosphere, 237 ml (0.237 mole) of a 1 M solution of borane-tetrahydrofuran complex was added during 30 minutes with stirring at −3° C. to a solution of 64.6 g (0.474 mole) of (−)-α-pinene in 100 ml of tetrahydrofuran, and the reaction mixture was stirred for an additional 30 minutes. A solution of 22.8 g (0.119 mole) of 7-phenyl-1H-indene in 100 ml of tetrahydrofuran was added dropwise, and stirring was continued for an additional 4 hours at −3° C. Water (46.5 ml) was added, and stirring and cooling were continued for an additional 30 minutes. A 3 N aqueous solution of sodium hydroxide (118.6 ml) was added, and stirring and cooling were maintained for an additional 30 minutes. The mixture was allowed to warm to about 5° C., and 120.4 ml of a 30% hydrogen peroxide solution was added over 30 minutes. The mixture was allowed to warm to room temperature and was stirred for about 16 hours. Solid was collected by filtration and was washed with two portions of 300 ml each of diethyl ether. The ether wash was combined with the filtrate, and the aqueous and organic layers were separated. The aqueous phase was saturated with sodium chloride and extracted with 200 ml of diethyl ether. The ether extract was added to the organic phase from above, and the whole was then dried, filtered, and the filtrate concentrated to give an oil. The oil was distilled using a Kugelrohr distillation apparatus (80° C./0.05 mm Hg) to leave 22.1 g of an oily pot residue containing a mixture of 4-phenyl-2-indanol, 4-phenyl-1-indanol, and 7-phenyl-1H-indene.

In the following step, the 4-phenyl-1-indanol component of the product mixtures is converted to 7-phenyl-1H-indene, and 4-phenyl-2-indanol is then separated from the mixture by chromatography.

B. Separation and refinement of (−)-4-phenyl-2-indanol

A stirred solution of the oily residue from above and 22.1 g of p-toluenesulfonic acid monohydrate in 200 ml of toluene was heated at reflux for one-half hour under a Dean-Stark trap. The reaction mixture was cooled, and the whole applied to a column of 125 g of silica gel. Elution was accomplished with toluene, then with ethyl acetate, to give, from appropriate ethyl acetate fractions, 12.4 g of (−)-4-phenyl-2-indanol as an oil.

The 12.4 g of oil was crystallized from 35 ml of cold toluene to give 6.2 g of product, mp 101°-103° C. The 6.2 g of crystalline material was added to 17 ml of toluene, and the mixture was stirred at room temperature for about 16 hours. The insoluble material was collected on a filter paper to give 4.0 g of (−)-4-phenyl-2-indanol, mp 104°-105° C., EE≧95%.

Examples 4–8 pertain to the preparation of 1R,cis-3-(2-chloro-3,3,3-trifluoro-1-propenyl)-2,2-dimethylcyclopropanecarbonyl chloride and intermediates therefor.

EXAMPLE 4

Synthesis of Ethyl 3,3-Dimethyl-4,6,6-Trichloro-7,7,7-Trifluoroheptanoate

A stirred solution of 44.6 g (0.267 mole) of ethyl 3,3-dimethyl-4-pentenoate, 100 g (0.533 mole) of 1,1,1- trichlorotrifluoroethane, 0.27 g (0.0027 mole) of cuprous chloride, and 8.2 g (0.134 mole) of ethanolamine in 270 ml of tertiary butyl alcohol, under a nitrogen atmosphere, was heated at reflux for 16 hours. The reaction mixture was cooled to ambient temperature and extracted with three portions of 100 ml each of diethyl ether. A precipitate formed in the extracts, and was removed by vacuum filtration. The filter cake was washed with two portions of 25 ml each of diethyl ether. The ether extracts were combined with the washings, and the whole was concentrated under reduced pressure to give an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87° at 0.12–0.15 mm. The nmr spectrum was consistent with the assigned structure. The corresponding methyl ester may be prepared by an analogous method.

EXAMPLE 5

Synthesis of Methyl Cis,Trans-3-(2-Chloro-3,3,3-Trifluoro-1-Propenyl)-2,2-Dimethylcyclopropanecarboxylate A. Preparation of methyl cis,trans-3-(2,2-dichloro-3,3,3-trifluoropropyl)-2,2-dimethylcyclopropanecarboxylate A stirred solution of 37.0 g (0.112 mole) of methyl 3,3-dimethyl-4,6,6-trichloro-7,7,7-trifluoroheptanoate, 50 ml of tert-butyl alcohol, 50 ml of dimethylformamide, and 50 ml of hexane, under an argon atmosphere, was cooled to $-5°$ C. To the stirred solution was added dropwise a solution of 16.4 g (0.14 mole) of potassium tert-butoxide in 200 ml of tert-butyl alcohol at such a rate so as to maintain the reaction mixture temperature at $-3°$ to $-5°$ C. Upon complete addition, the reaction mixture was stirred for 4 hours at $-3°$ to $-5°$ C., then poured into a solution of 8.0 g of ammonium chloride in 250 ml of water. The mixture was extracted with two portions of 200 ml each of diethyl ether. The combined ether extracts were washed with two portions of 200 ml each of water. The ether layer was dried with sodium sulfate, filtered, and the filtrate evaporated under reduced pressure to give a residual oil. The oil was distilled under reduced pressure to give 19.8 g of methyl cis,trans-3-(2,2-dichloro-3,3,3-trifluoropropyl)-2,2-dimethylcyclopropanecarboxylate; b.p. 55°–57° C./0.09 mm Hg. The ir and the nmr spectra were consistent with the proposed structure.

Analysis calc'd for $C_{10}H_{13}Cl_2F_3O_2$: C 40.98; H 4.47; Found: C 41.50; H 4.41

B. Preparation of methyl cis,trans-3-(2-chloro-3,3,3-trifluoro-1-propenyl)-2,2-dimethylcyclopropanecarboxylate A stirred solution of 30.6 g (0.105 mole) of methyl cis,trans-3-(2,2-dichloro-3,3,3-trifluoropropyl)-2,2-dimethylcyclopropanecarboxylate and 17.6 g (0.116 mole) of 1,5-diazabicyclo[5.4.0]undec-5-ene in 100 ml of dimethylformamide was heated at 100° C. for 4 hours. The reaction mixture was cooled and poured into a solution of 37.2 ml of concentrated hydrochloric acid in 300 ml of water. The mixture was extracted with three portions of 200 ml each of diethyl ether. The ether extracts were combined and washed with an aqueous saturated solution of sodium chloride. The ether layer was dried with sodium sulfate, filtered, and the filtrate evaporated under reduced pressure to give a residual oil. The oil was dissolved in hexane, treated with decolorizing carbon, and filtered. The filtrate was evaporated under reduced pressure to a residual oil. The oil was distilled under reduced pressure to give, in three fractions, 10.0 g of the racemic compound methyl cis,trans-3-(2-chloro-3,3,3-trifluoro-1-propenyl)-2,2-dimethylcyclopropanecarboxylate, b.p. 40°–60° C./0.05 mm. The ir and the nmr spectra were consistent with the proposed structure. The nmr spectra indicated an 88:12 mixture of cis:trans isomers.

Analysis calc'd for $C_{10}H_{12}ClF_3O_2$: C 46.80; H 4.71; Found: C 46.91; H 4.79.

EXAMPLE 6

Synthesis of Cis-3-(2-Chloro-3,3,3-Trifluoro-1-Propenyl)-2,2-Dimethylcyclopropanecarboxylic Acid A stirred solution of 90.0 g (0.35 mole) of methyl cis,trans-3-(2-chloro-3,3,3-trifluoro-1-propenyl)-2,2-dimethylcyclopropanecarboxylate (approximately 90% cis, prepared in accordance with Example 5B), 5.4 ml of concentrated sulfuric acid, and 13.8 ml of water in 138 ml of acetic acid was heated under reflux for 1 hour. The reaction mixture was cooled and extracted with two portions of 100 ml each of diethyl ether. The combined extracts were dried with sodium sulfate, filtered, and the filtrate concentrated under reduced pressure to give a solid residue. The residue was digested with 300 ml of hexane, and the hexane solution was decanted from a dark, tarry residue and allowed to cool to ambient temperature. A solid precipitate formed and was collected by filtration to give 42.4 g of the racemic compound cis-3-(2-chloro-3,3,3-trifluoro-1-propenyl)-2,2-dimethylcyclopropanecarboxylic acid, as determined by nmr spectroscopy. A melting point was not determined. The melting point of another sample of cis acid prepared at a different time was 108°–110° C.

EXAMPLE 7

Resolution of Cis-3-(2-Chloro-3,3,3-Trifluoro-1-Propenyl)-2,2-Dimethylcyclopropanecarboxylic Acid A stirred solution of 15.0 g (0.062 mole) of racemic cis-3-(2-chloro-3,3,3-trifluoro-1-propenyl)-2,2-dimethylcyclopropanecarboxylic acid in 250 ml of toluene was warmed to 50°–60° C., and 8.5 g (0.070 mole) of (−)-α-phenylethylamine was added dropwise during 30 minutes. Upon complete addition, the reaction mixture was allowed to cool to ambient temperature and stand for 16 hours. A solid was collected by vacuum filtration, 16.7 g, m.p. 167°–172° C. The solid was dissolved in 100 ml of hot ethanol, and the solution was allowed to cool slowly to room temperature, then was placed in a refrigerator. After precipitation was complete, a crystalline solid was collected by vacuum filtration to give 7.6 g of material, m.p. 174°–175° C. The mother liquor was set aside. The solid was recrystallized from 65 ml of hot ethanol to give 2.1 g of the amine salt of 1R,cis-3-(2-chloro-3,3,3-trifluoro-1-propenyl)-2,2-dimethylcyclopropanecarboxylic acid, m.p. 175°–176.5° C. The mother liquor was combined with the mother liquor from above and was set aside for later use. The salt was suspended in 50 ml of diethyl ether, and the mixture was extracted with 40 ml of 0.5 N sodium hydroxide. The two phases were separated, and the aqueous layer was acidified with 15 ml of 2 N hydrochloric acid, then extracted with two portions of 25 ml each of diethyl ether. The ether extracts were combined with the organic phase from above, and the whole was dried with magnesium sulfate, filtered and the filtrate concentrated under reduced pressure to give 1.2 g of 1R,cis-3-(2-chloro-3,3,3-trifluoro-1-propenyl)-2,2-dimethylcyclopropanecarboxylic acid; m.p. 112°–112.5° C.; optical purity, at least 95%.

The combined mother liquors that had been set aside above and similar fractions from a previous run were combined and concentrated to dryness under reduced pressure. The residue was treated with 200 ml of aqueous 0.5 N sodium hydroxide, and the whole was extracted with diethyl ether. The ether extract was discarded. The aqueous layer was made acidic with aqueous 2 N hydrochloric acid and extracted with diethyl ether. The ether extract was concentrated to dryness under reduced pressure, and the residue was dissolved in 200 ml of hot heptane. The heptane solution was allowed to cool to ambient temperature, than was placed in a refrigerator. The resulting white precipitate was collected by filtration to give 24.3 g of 1S-enriched cis acid, m.p. 97°–101° C.

The 24.3 g (0.10 mole) of 1S-enriched cis acid was stirred at 50°–60° C. in 500 ml of toluene, and 13.3 g (0.11 mole) of (+)-α-phenylethylamine in 50 ml of toluene was added. Upon complete addition, the reaction mixture was stirred for 1.5 hours at 50°–60° C., then was allowed to stand at ambient temperature for 16 hours. The resulting precipitate, collected by filtration, weighed 20.2 g, m.p. 169°–171° C. Recrystallization twice from absolute ethanol gave 11.2 g, m.p. 176°–177° C.

The 11.2 g of solid was added to 200 ml of diethyl ether, and the mixture was extracted with 100 ml of aqueous 0.5 N sodium hydroxide. The two phases were separated, and the aqueous layer was acidified with aqueous 2 N hydrochloric acid and extracted with diethyl ether. The ether extract was dried with magnesium sulfate, filtered, and the filtrate was concentrated under reduced pressure to give 5.2 g of 1S,cis-3-(2-chloro-3,3,3-trifluoro-1-propenyl)-2,2-dimethylcyclopropanecarboxylic acid; m.p. 112°–113° C.; optical purity, at least 95%.

The optical purity of the 1R,cis and 1S,cis acids was determined by nmr spectral analyses conducted in the presence of a chiral shift reagent, tris-(3-heptafluorobutyryl-d-camphorato), europium (III) derivative, in accordance with the methods set forth in H. L. Goering et al., *J. Am. Chem. Soc.*, 96, 7842 (1974) and E. L. Plummer et al., *J. Chem. Ecol.*, 2 307 (1976).

EXAMPLE 8

Synthesis of 1R,Cis-3-(2-Chloro-3,3,3-Trifluoro-1-Propenyl)-2,2-Dimethylcyclopropanecarbonyl Chloride A stirred solution of 1.0 g (0.004 mole) of 1R,cis-3-(2-chloro-3,3,3-trifluoro-1-propenyl)-2,2-dimethylcyclopropanecarboxylic acid in 50 ml of toluene was warmed to 60° C., and 1.0 g (0.008 mole) of oxalyl chloride was added. The reaction mixture was heated at 60° C. for 5.25 hours, then cooled to ambient temperature. The reaction mixture was concentrated under reduced pressure to give a residual oil. The oil was dissolved in 15 ml of dry toluene, and the solution was concentrated under reduced pressure to give 1.0 g of 1R,cis-3-(2-chloro-3,3,3-trifluoro-1-propenyl)-2,2-dimethylcyclopropanecarbonyl chloride as an oil. The oil was used in subsequent reactions without further purification.

Examples 9–11 illustrate the preparation of compounds of formula I.

EXAMPLE 9

Synthesis of (−)-4-Phenyl-2-Indanyl 1R,Cis-3-(2-Chloro-3,3,3-Trifluoro-1-Propenyl)-2,2-Dimethylcyclopropanecarboxylate A stirred solution of 1.0 g (0.004 mole) of 1R,cis-3-(2-chloro-3,3,3-trifluoro-1-propenyl)-2,2-dimethylcyclopropanecarbonyl chloride, 0.8 g (0.004 mole) of (−)-4-phenyl-2-indanol (EE≧95%) and 0.3 ml (0.004 mole) of pyridine in 25 ml of toluene was heated at 50° C. for one hour. The reaction mixture was cooled to ambient temperature and washed with 50 ml of aqueous 2 N hydrochloric acid, then with 35 ml of an aqueous saturated solution of sodium chloride. The organic layer was dried with magnesium sulfate, filtered, and the filtrate was subjected to column chromatography on silica gel. Elution was accomplished using toluene. The appropriate fractions were combined and concentrated under reduced pressure to give 0.9 g of (−)-4-phenyl-2-indanyl 1R,cis-3-(2-chloro-3,3,3-trifluoro-1-propenyl)-2,2-dimethylcyclopropanecarboxylate. The nmr spectrum was consistent with the proposed structure.

nmr (CDCl$_3$, TMS internal standard, ppm): 1.23 (6H,s), 1.82–2.34 (2H,m), 2.83–3.50 (4H, octet), 5.40–5.72 (1H,m), 6.87–7.03 (1H,d), 7.20–7.47 (7H,m).

EXAMPLE 10

Synthesis of (+)-4-Phenyl-2-Indanyl 1R,Cis-3-(2-Chloro-3,3,3-Trifluoro-1-Propenyl)-2,2-Dimethylcyclopropanecarboxylate In the manner of Example 9, 0.8 g (0.004 mole) of (+)-4-phenyl-2-indanol, EE≧95% (which may be prepared as described in Example 2), was combined with 1.0 g (0.004 mole) of 1R,cis-3-(2-chloro-3,3,3-trifluoro-1-propenyl)-2,2-dimethylcyclopropanecarbonyl chloride in the presence of 0.3 ml (0.004 mole) of pyridine and 25 ml of toluene to give 1.27 g of (+)-4-phenyl-2-indanyl 1R,cis-3-(2-chloro-3,3,3-trifluoro-1-propenyl)-2,2-dimethylcyclopropanecarboxylate. The nmr spectrum was consistent with the proposed structure.

EXAMPLE 11

Synthesis of (±)-4-Phenyl-2-Indanyl 1R,Cis-3-(2-Chloro-3,3,3-Trifluoro-1-Propenyl)-2,2-Dimethylcyclopropanecarboxylate In the manner of Example 9, 0.8 g (0.004 mole) of racemic 4-phenyl-2-indanol (which may be prepared as described in Example 1) was combined with 1.0 g (0.004 mole) of 1R,cis-3-(2-chloro-3,3,3-trifluoro-1-propenyl)-2,2-dimethylcyclopropanecarbonyl chloride in the presence of 0.3 ml (0.004 mole) of pyridine and 25 ml of toluene to give 1.0 g (±)-4-phenyl-2-indanyl 1R,cis-3-(2-chloro-3,3,3-trifluoro-1-propenyl)-2,2-dimethylcyclopropanecarboxylate. The nmr spectrum was consistent with the proposed structure.

In the method aspect of this invention, an effective insecticidal or acaricidal amount of the compound of formula I is applied to the locus where control is desired, i.e., to the insect or acarid itself or to the foliage or seeds of agricultural plants. The compounds are useful for the control of household, veterinary, and crop pests of the phylum Arthropoda, and may be applied as technical material or as formulated product. Typical formulations include compositions of the active ingredient in combination with an agriculturally acceptable carrier or extender, preferably with a surface active agent, and optionally with other active ingredient. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90% or 95%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.001% to about 50%, preferably up to about 10% by weight.

Many variations of spraying, dusting, and controlled or slow release compositions of a type known in the art may be used by substituting or adding an insecticidal compound or compounds of this invention into the compositions known or apparent to the art.

The insecticidal or acaricidal compounds of this invention may be formulated and applied with other compatible active agents including nematicides, insecticides, acaricides, fungicides, plant regulators, herbicides, fertilizers, and the like.

In applying these compounds, whether alone or with other agricultural chemicals, an effective insecticidal or acaricidal amount of the active ingredient must be applied. While the application rate will vary widely depending on the choice of compound, formulation, mode of application, plant species being protected, planting density and other like factors, a suitable use rate for agricultural crops may be in the range of 0.005 to 3 k/ha, preferably 0.01 to about 1 k/ha.

The insecticidal or acaricidal compounds of this invention were tested for pesticidal activity as described in Examples 12 and 13.

EXAMPLE 12

Foliar Application Test

In this test, the compounds of the present invention were tested for pesticidal efficacy on green plant foliage against the representative species Mexican bean beetle (*Epilachna varivestis* Muls.), pea aphid (*Acyrthosiphon pisum* [Harris]), southern armyworm (*Spodoptera eridania* [Cram.]), and twospotted spider mite (*Tetranychus urticae* [Koch]), which are identified in the table below by the abbreviations MBB, PA, SAW, and TSM respectively.

The compounds were applied in solution form, the solution being composed of 1250 ppm of the test compound, 10% acetone, 0.25% octylphenoxypolyethoxyethanol, and water.

The activity against Mexican bean beetle and southern armyworm was evaluated by spraying the upper and lower surfaces of the leaves of pinto bean plants with a solution of 1250 ppm of test compound. The leaves were sprayed to run-off, then were allowed to dry. After the leaves had dried, they were excised from the plants and placed in 240 ml or 480 ml containers. Ten 3rd instar larvae of the appropriate species were placed in each container, which was then capped to prevent escape of the insects from the test site. Two replicates of ten insects each were used. The tests were kept in a holding room at 80° C. and 50% relative humidity for 48 hours, and the percent mortality was determined.

The activity against pea aphid was determined by the same procedure as that just described except that broad bean plants were used and the leaves were infested with adult aphids.

The activity against twospotted spider mite was evaluated in the following manner. Sections of pinto bean leaves containing approximately 75 adult mites each were placed on uninfested pinto bean plants, and the plants were then sprayed with a solution of 1250 ppm of test compound. Percent mortality was determined after 48 hours at 80° C. and 50% relative humidity. Two replicates for each test compound were used.

For comparison purposes, compounds corresponding to those of Examples 9 and 11 but having the 1S,cis acid moiety, rather than 1R,cis, were included in the test.

The results of the test, given in the following table, show the present compounds to be highly active against both insects and mites and the comparison compounds (having the 1S,cis acid moiety) to be inactive at the testing level used.

Foliar Application

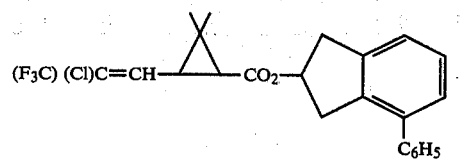

| Cpd of Example | Isomer Content | | % Mortality at 1250 ppm | | | |
|---|---|---|---|---|---|---|
| | Alcohol Moiety | Acid Moiety | MBB | PA | SAW | TSM |
| — | (−); EE ≥ 95% | 1S,cis | 0 | 0 | 0 | 0 |
| 9 | (−); EE ≥ 95% | 1R,cis | 70 | 100 | 100 | 100 |
| 10 | (+); EE ≥ 95% | 1R,cis | 100 | 100 | 100 | 100 |
| — | racemic | 1S,cis | 0 | 0 | 0 | 0 |
| 11 | racemic | 1R,cis | 100 | 100 | 100 | 100 |

EXAMPLE 13

Topical Application Test Comparative Activity

The compounds included in this test were the compounds of Examples 10 and 11 and two corresponding compounds bearing a racemic cis acid moiety. The compounds were tested separately and at different times. Thus, the comparisons shown in the table below are comparisons of data from separate tests and are not side-by-side comparisons.

Two replicates of ten larvae of each test insect species were employed for each test compound. A 9 cm petri dish lined with a piece of filter paper, and containing a food source was employed for each replicate. A one microliter droplet of a solution of test compound in acetone was applied to the second or third dorsal thoracic segment of each larvae. A series of concentrations were used so that LD$_{50}$ values could be determined. Mortality data were collected twenty-four hours after application of the toxicant solution. Relative potency, based on a value of 1.0 for each compound having the racemic cis acid moiety, was determined by a comparison of LD$_{50}$ values.

The insect species employed in this test were southern armyworm (*Spodoptera eridania* [Cram.]), Mexican bean beetle (*Epilachna varivestis* Muls.), milkweed bug (*Oncopeltus faciatus* [Dallas]), cabbage looper (*Trichoplusia ni* [Hubner]), and tobacco budworm (*Heliothis virescens* [Fabricius]), identified respectively in the table below as SAW, MBB, MWB, CL, and TBW. With certain exceptions, the present compounds exhibited higher activity in this test than the corresponding compounds having the racemic cis acid moiety. Overall, the compound of Example 10 was about 2.0 times as active, and that of Example 11 about 1.9 times as active, as the corresponding racemic-cis-acid esters.

Topical Application Comparative Activity

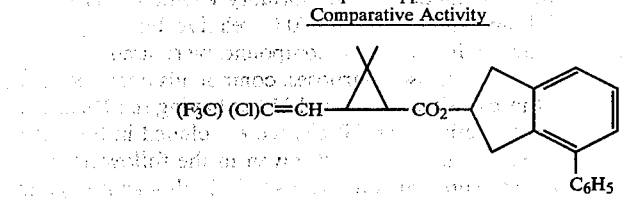

| Cpd of Example | Isomer Content | | Relative Potency | | | | | |
|---|---|---|---|---|---|---|---|---|
| | Alcohol Moiety | Acid Moiety | SAW | MBB | MWB | CL | TBW | Avg |
| — | (+); EE ≧ 95% | racemic cis | 1.0 | 1.0 | 1.0 | 1.0 | 1.0 | 1.0 |
| 10 | (+); EE ≧ 95% | 1R,cis | 2.2 | 0.6 | 0.2 | 4.8 | 2.4 | 2.0 |
| — | racemic | racemic cis | 1.0 | 1.0 | 1.0 | 1.0 | 1.0 | 1.0 |
| 11 | racemic | 1R,cis | 3.8 | 1.1 | 1.0 | 2.3 | 1.2 | 1.9 |

I claim:
1. A 4-phenyl-2-indanyl 1R,cis-3-(2-halo-3,3,3-trifluoro-1-propenyl)-2,2-dimethylcyclopropanecarboxylate of the formula

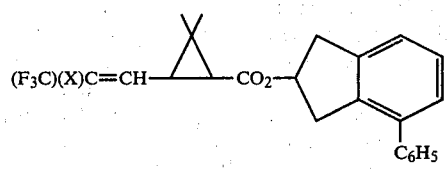

wherein X is a halogen atom.

2. The compound of claim 1 wherein the 4-phenyl-2-indanyloxy moiety is racemic.

3. The compound of claim 1 wherein the 4-phenyl-2-indanyloxy moiety is dextrorotatory, the dextrorotatory isomer being present in an enantiomeric excess of at least 25% over the levorotatory isomer.

4. The compound of claim 3 wherein the enantiomeric excess of the dextrorotatory isomer over the levorotatory isomer is at least 60%.

5. The compound of claim 1 wherein the 4-phenyl-2-indanyloxy moiety is levorotatory, the levorotatory isomer being present in an enantiomeric excess of at least 25% over the dextrorotatory isomer.

6. The compound of claim 5 wherein the enantiomeric excess of the levorotatory isomer over the dextrorotatory isomer is at least 60%.

7. The compound of any one of claims 1–6 wherein X is a chlorine atom.

8. The compound (±)-4-phenyl-2-indanyl 1R,cis-3-(2-chloro-3,3,3-trifluoro-1-propenyl)-2,2-dimethylcyclopropanecarboxylate.

9. The compound (+)-4-phenyl-2-indanyl 1R,cis-3-(2-chloro-3,3,3-trifluoro-1-propenyl)-2,2-dimethylcyclopropanecarboxylate.

10. The compound (−)-4-phenyl-2-indanyl 1R,cis-3-(2-chloro-3,3,3-trifluoro-1-propenyl)-2,2-dimethylcyclopropanecarboxylate.

* * * * *

UNITED STATES PATENT AND TRADEMARK OFFICE
CERTIFICATE OF CORRECTION

PATENT NO. : 4,429,149
DATED      : January 31, 1984
INVENTOR(S): John Francis Engel It is certified that error appears in the above—identified patent and that said Letters Patent is hereby corrected as shown below:

Column 1, line 11, "No. 043,372," should read --No. 042,372.--.
Column 3, line 26, "spura, or" should be --supra, or--.

Signed and Sealed this

Sixth Day of November 1984

[SEAL]

Attest:

GERALD J. MOSSINGHOFF

Attesting Officer

Commissioner of Patents and Trademarks